Figure 1:
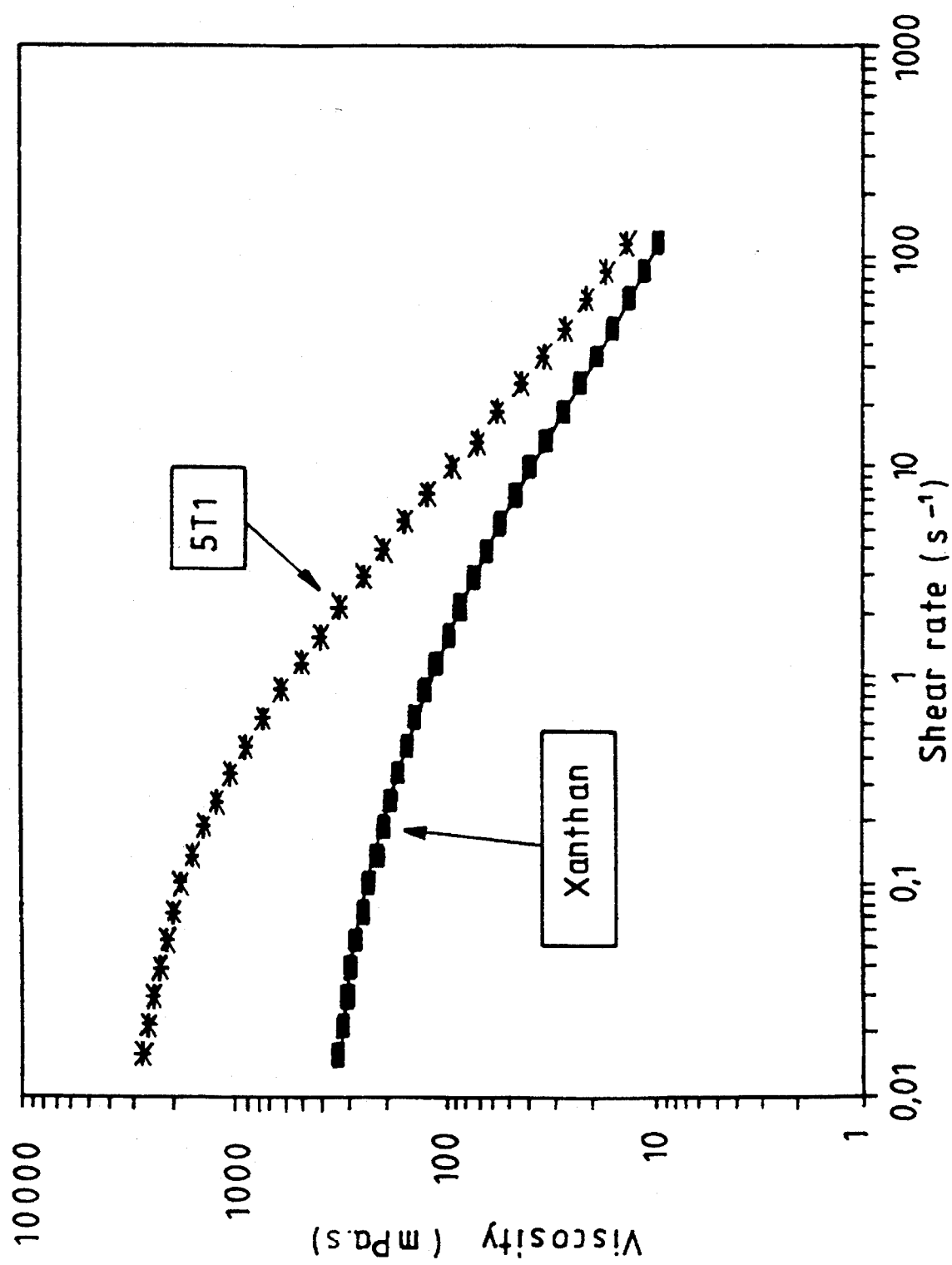

United States Patent [19]

Fontaine et al.

[11] Patent Number: 5,455,343

[45] Date of Patent: Oct. 3, 1995

[54] POLYSACCHARIDE, ITS APPLICATIONS, ITS PRODUCTION BY FERMENTATION AND THE PSEUDOMONAS STRAIN WHICH PRODUCES IT

[75] Inventors: Thierry Fontaine, La Barre De Semilly; Bernard Fournet, Villeneuve D'Asq; Marie France Planard, Carentan, all of France

[73] Assignee: Elf Sanofi, Paris, France

[21] Appl. No.: 949,263

[22] Filed: Sep. 24, 1992

[30] Foreign Application Priority Data

Sep. 25, 1991 [FR] France ................................. 91 11823

[51] Int. Cl.⁶ .................................................. C12P 19/04
[52] U.S. Cl. ........................ 536/123.1; 536/123; 435/101
[58] Field of Search ................................... 536/114, 123, 536/123.1; 435/101

[56] References Cited

FOREIGN PATENT DOCUMENTS

| 0001895 | 5/1979 | European Pat. Off. . |
| 0023397 | 2/1981 | European Pat. Off. . |
| 0410604 | 1/1991 | European Pat. Off. . |
| 2058812 | 4/1981 | United Kingdom . |

*Primary Examiner*—Douglas W. Robinson
*Assistant Examiner*—Kathleen Kahler Fonda
*Attorney, Agent, or Firm*—Jacobson, Price, Holman & Stern

[57] ABSTRACT

This polysaccharide consists of repeating units which are composed of a backbone, comprising 2 radicals of D-mannose, 2 of D-glucose, 1 of D-galactose, 1 of D-glucuronic acid, 1 of D-xylose, 1 of L-lyxose and 1 of L-fucose, on which pyruvic acid groups may be grafted and of which certain of the saccharide hydroxyl groups are esterified as acetate. It can be employed as a viscosity agent for thickening and gelling.

6 Claims, 2 Drawing Sheets

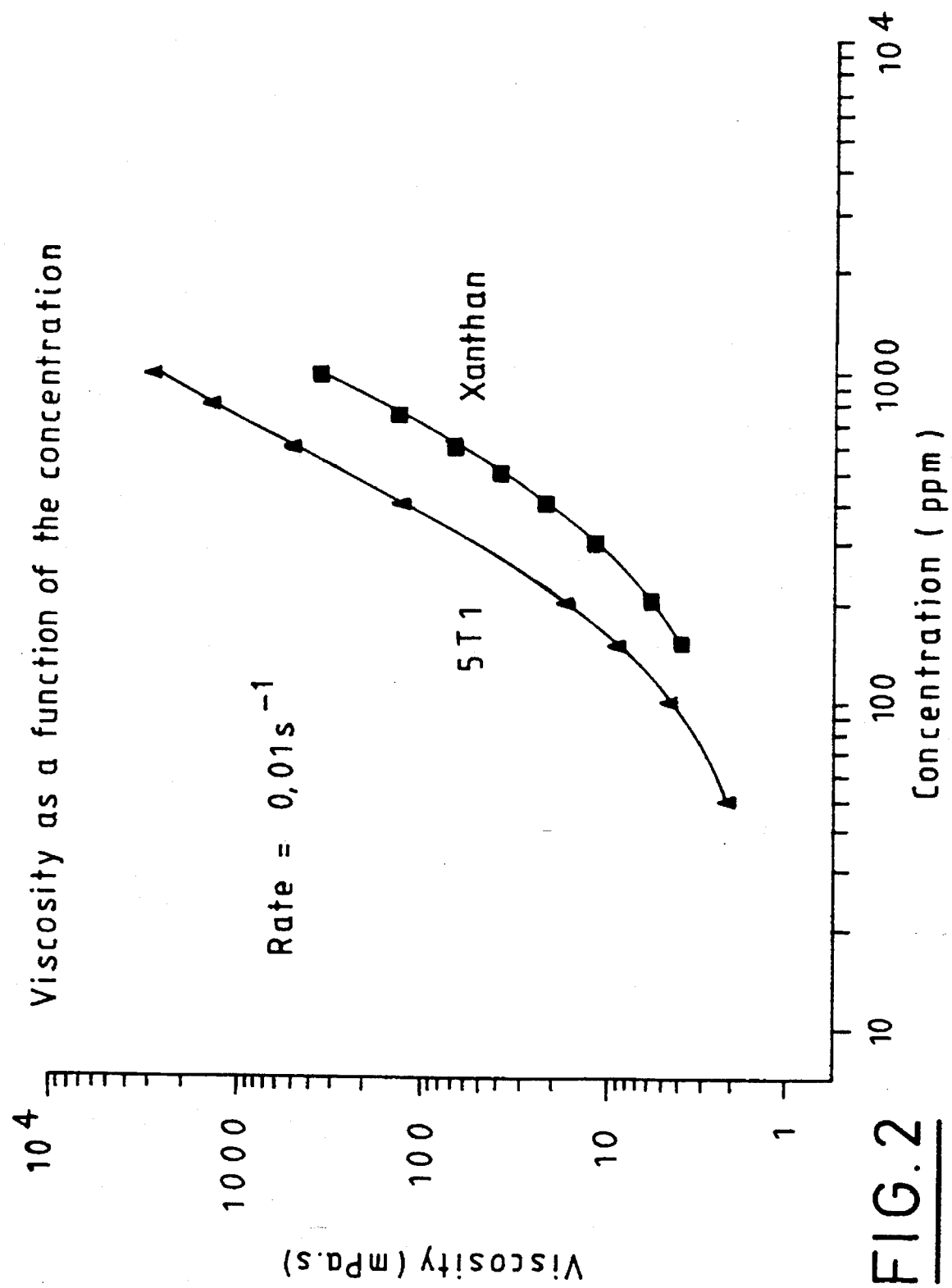

POLYSACCHARIDE, ITS APPLICATIONS, ITS PRODUCTION BY FERMENTATION AND THE PSEUDOMONAS STRAIN WHICH PRODUCES IT

The present invention relates to a new polysaccharide, to the process for obtaining it by the culturing of a microorganism of the Pseudomonas genus and to this microorganism, and to the applications of this polysaccharide as a viscosity agent for thickening, gelling or stabilising suspensions.

Polysaccharides produced by various species of microorganisms are known and the particular rheological properties of these polysaccharides enable them to be used as suspending agents or as thickening or gelling agents for aqueous media; xanthan, for example, goes into the composition of inks, paints, food products or medicines; scleroglucan is employed in oil drilling.

A microorganism strain of the Pseudomonas genus has now been isolated from a sample of soil from Normandy which, by culturing in a conventional nutrient medium containing sources of organic carbon and nitrogen and inorganic salts, secretes a new polysaccharide whose rheological properties in aqueous medium are particularly advantageous and are of the same type as those of xanthan but corresponds to much lower concentration.

According to a first aspect, the invention therefore relates to a bacterial strain called PS-5T1, a sample of which was deposited on 24th Sep. 1991 in the Collection Nationale de Cultures de Microorganismes (CNCM)—Paris, France under the number I-1145, in compliance with the Treaty of Budapest.

The PS-5T1 bacteria are gram-negative; they are rod-shaped with a mean size of 0.7 to 0.8 μm by 1.1 to 1.45 μm.

The strain, on agar nutrient medium Plate Count Agar marketed by DIFCO, forms round, domed, yellow and shiny colonies which reach 2 mm in diameter after 48 hours at 28° C. On MY agar medium (DIFCO), the appearance of the colonies is identical and their diameter increases if incubation is continued.

The physiological and biochemical properties of the PS-5T1 bacteria, determined according to the methods described in Bergey's Manual, Noel R. Krieg et al., 1974 and—The Prokaryotes, Mortimer P. Starr, 1981, are represented in Table I.

TABLE I

| | |
|---|---|
| Cytochrome oxidase | + |
| Catalase | + |
| Oxidation-fermentation test | oxidation |
| Anaerobic culture | − |
| Growth at various NaCl concentrations: | |
| 0.5% | + |
| 1.0% | + |
| 2.0% | + |
| 2.5–6.0% | − |
| Surviving at 60° C. for 30 min: | + |
| $10^2$ cells/ml from $10^9$ cells | |
| Growth at various temperatures: | |
| 4° C. | − |
| 20° C. | + |
| 30° C. | + |
| 32° C. | − |
| 37–40–50° C. | − |
| Growth in the presence of triphenyltetrazolium at | |
| 0.01% | + |
| 0.02% | + |

TABLE I-continued

| | |
|---|---|
| 0.05% | − |
| 0.1% | − |
| Growth at various pHs | |
| 4; 5; 5.5 | − |
| 6.5; 7; 7.5 | + |
| 8–9 | + |
| 10 to 12 | − |
| Growth on Triple sugar iron agar | |
| Slant (of the inclined tube) | colour change |
| Deposit | − |
| Gas production | − |
| $H_2S$ production | − |
| Pigment on King A medium | − |
| Pigment on King B medium | − |
| Growth on Burk's medium | − |
| Take up of malonate | − |
| Hydrolysis of cellulose | − |
| Hydrolysis of pectin | − |
| Denitrification test | − |

Table II indicates the results of conventional enzymatic tests carried out using all the reactants marketed by the Company API System, la Balme-les-Grottes 38390—Montalieu Vercieu (FR).

TABLE II

| | |
|---|---|
| Indole | − |
| Voges-Proskauer (VP) | + |
| Simmons' citrate | + |
| Nitrate reduction | + |
| Arginine dihydrolase | − |
| Lysine decarboxylase | − |
| Ornithine decarboxylase | − |
| $H_2S$ production | − |
| Urease test | − |
| Egg Yolk reaction (lecithinase) | − |
| Hydrolysis of starch | + |
| Hydrolysis of gelatin | + |
| Protease | + |

The polysaccharide according to the invention may be obtained by fermentation of these bacteria in a suitable culture medium, which is stirred and aerated in the conventional way.

The PS-5T1 bacteria do not grow on a medium containing an ammonium salt as the only source of nitrogen, but the nitrogen source present in the fermentation medium may be of various protein origins, such as, for example, yeast extracts, soya flours, corn steep liquors, gelatin, distillery draffs or peptones. These proteins are introduced at a concentration of 0.1% to 1% (w/v) in the aqueous liquid medium, which corresponds to an equivalent weight of total nitrogen of approximately 0.16 to 1.6 g/l.

The bacteria are able to employ a great number of carbohydrates as a carbon source, for example, galactose, glucose, mannose, amygdalin, cellobiose, maltose, starch, glycogen and lactose and the nutrient medium may contain a single one of these compounds or a mixture thereof. Generally, from 2% to 6% (w/v) thereof is introduced into the aqueous fermentation medium.

There will be chosen, from the growth factor inorganic salts which can be used for the culturing of the PS-5T1 bacteria, the salts providing Na, K, $NH_4$, Ca, Mg, $PO_4$, $SO_4$, Cl, or $CO_3$ ions. Trace elements, such as Cu, Mn, Fe or Zn, are also preferably introduced into the nutrient medium, in a conventional way, at a concentration of a few ppm.

The fermentation which makes it possible to produce the polymer of the invention can be carried out in stirred and aerated medium at a temperature of between 20° C. and 32° C., and preferably at 28° C.; the pH of the medium is

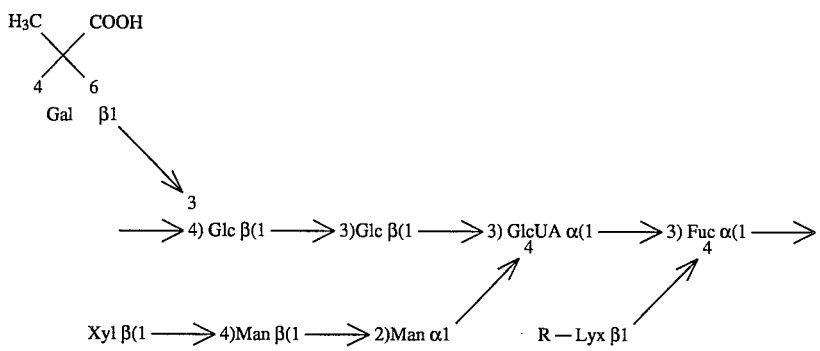

between 6.5 and 9.0 and, preferably, towards 7.0 and it is adjusted, if necessary, during the fermentation. A fermentation lasts from 30 hours to 80 hours before the medium becomes too thick.

The polysaccharide is isolated from the fermentation medium at the end of culturing, preferably by precipitation; in order to do this, there is introduced into the medium, after its sterilisation, a water-miscible solvent in which the polymer is insoluble, such as an alcohol such as ethanol, methanol and, preferably, isopropanol, or a ketone, such as acetone; the crude polysaccharide, coprecipitated with cell bodies and salts, is isolated in this way; the polysaccharide is said to be in the native form.

It can be employed as it is or after purification, especially by dialysis, to remove the salts, and by reprecipitation from an aqueous solution of low concentration, 1 to 5 g/l or, preferably, 2 to 3 g/l, by addition of one of the abovementioned solvents, generally by addition of isopropanol.

In order to improve its dispersibility in aqueous medium, the polymer of the invention may be treated with an aliphatic dialdehyde, such as glutaraldehyde, as is done for other polysaccharides.

Another subject matter of the invention is the polysaccharide, named 5T1, in its various forms, which may be obtained by culturing the PS-5T1 bacteria, characterised in that it consists of repeating units, the backbone of each of which is composed of 2 radicals of D-mannose, 2 of D-glucose, 1 of D-galactose, 1 of D-glucuronic acid, 1 of D-xylose, 1 of L-lyxose and 1 of L-fucose, and of which certain saccharide hydroxyls are optionally esterified, especially as acetate form.

Depending on the culturing and isolation conditions, the polysaccharide may have various forms, that is to say, may carry more or less acetate and pyruvate groups on the backbone.

The structure and the sequence of each unit of the polysaccharide were determined from a substantially homogeneous mass sample using conventional analytical techniques and, more particularly, a form of the 5T1 polysaccharide consists of a succession of nonasaccharide groups whose base backbone, on which a pyruvic group is grafted, is represented by the following structural formula I in which R, which is optionally present on the lyxose, represents a $C_1$–$C_6$ group:

In a particular form, the 5T1 polysaccharide consists of the product of formula I on which are bound three acetate groups.

The rheological properties of the new polymer according to the invention are particularly advantageous:

significant solubility at ambiant temperature, compatibility with milk, it has a yield value, in solution, the polymer according to the invention has a viscosity greater than that of xanthan. The viscosity of a 1% solution is stable even in an acid medium, such as in 20% acetic acid, or in the presence of a salt, such as NaCl, $Na_2SO_4$ or $CaCl_2$ and does not change when the temperature of the solution is raised from 20° C. to 90° C. but disappears at pH>10, the 5T1 polysaccharide gels in aqueous medium in the presence of a trivalent cation, such as $Al^{3+}$, $Fe^{3+}$or $Cr^{3+}$; a consistent gel is thus obtained with a 0.5% aqueous solution of the polymer containing 50 ppm of $Al^{3+,}$ 100 ppm of $Fe^{3+}$or 200 ppm of $Cr^{3+}$.

It may be employed alone or as a mixture with the other known thickening and gelling agents: carrageenan, xanthan, guar, carob, alginate, pectin or gelatin, for technical or food applications. In particular, it can be introduced into cosmetic, pharmaceutical or plant-protection compositions, into dyes for textile printing, in printing inks, paints, cements and in food compositions such as dressings, cream desserts, sweetened compositions containing fruits, particularly in combination with pectin, or milk compositions, in combination with carrageenan.

In that which follows, an example of the preparation of a polysaccharide according to the invention, methods for determining its structure and its rheological properties, and examples of application are described.

EXAMPLE 1

Pseudomonas bacteria of the I-1145 strain were cultured on a MY agar medium. After incubating for 48 hours at 28° C., the culture medium obtained was employed for culturing in 100 ml of MY broth in a flask and, after incubating for 24 hours at 38° C., it is introduced and cultured in 1000ml of the same broth; finally, after culturing for 12 hours, the bacteria finally obtained were introduced into 10 liters of a nutrient medium, suitable for the production of the 5T1 polysaccharide, composed of: glucose (35 g/l), soya flour (5 g/l), K$_2$HPO$_4$ (3 g/l), MgSO$_4$ (1 g/l), MnSO$_4$ (50 µg/l), FeSO$_4$ (50 µg/l), ZnSO$_4$ (50 µg/l) and CuSO$_4$ (50 µg/l), and the fermentation was carried out at 28° C. in stirred and aerated medium while the pH of the medium was maintained at 7. After approximately 50 hours, the mixture was maintained at 80° C. for 15 min for the so-called sterilisation operation. After returning to room temperature, 2.5 volumes of isopropanol were introduced into the medium in order to precipitate the 5T1 polysaccharide.

After drying towards 55° C., 20 g of the expected native polymer were isolated.

The polysaccharide thus obtained may be introduced into approximately 10 liters of distilled water and the suspension filtered through a layer of kieselguhr; by introducing 3 to 5 volumes of isopropanol into the filtrate, the so-called pure polysaccharide precipitated.

Properties of the 5T1 polysaccharide

Viscosimetric measurements were carried out at 20° C., for a standard xanthan and for the pure polysaccharide obtained according to the above example, in aqueous solution in the presence of potassium chloride (10 g/l), with a Rheomat LS 30 viscometer, marketed by the Company Contraves (FR), either at various shear rates with solutions containing 10 g/l or at the shear rate of 0.01 second$^{-1}$ for weak concentrations. The curves obtained are represented in the appended FIGS. 1 and 2.

The results of other measurements carried out using a Brookfield viscometer, LVF model, containing a spindle, reference 2 or 3, and rotating at 30 revolutions per minute, for solutions of various concentrations, optionally containing 10 g/l of potassium chloride, are represented in Table III:

TABLE III

| Concentration of the polymer (g/100 ml) | KCl | Spindle reference | Viscosity native product | (mPa) purified product |
| --- | --- | --- | --- | --- |
| 0.5 | − | 3 | 760 | 1200 |
| 0.5 | + | 3 | 1240 | 1640 |
| 0.2 | − | 2 | 190 | 280 |
| 0.2 | + | 2 | 240 | 350 |
| 0.075 | − | 2 | 44 | 62 |
| 0.075 | + | 2 | 46 | 70 |

Structural study

Saccharide fragments were obtained either by fragmentation with CH$_3$OH/HCl at 80° C. of the polymer, optionally pretreated and acetylated, or after hydrolysis with trifluoroacetic acid at 100° C., followed by a reduction and then by an acetylation; they were generally studied with a method combining gas phase chromatography and mass spectrometry The purified 5T1 polysaccharide obtained under the conditions of the above example was pretreated:

with lithium in ethylenediamine in order to degrade the uronic acids, with sodium metaperiodate before and after saponification, which only decomposes xylose, lyxose and mannose, with CrO$_3$ in acetic acid, which destroys the peracetylated saccharides in equatorial anomeric configuration, with a strong base in anhydrous medium (LiCH$_3$SC$^{31}$ in dimethyl sulphoxide) which degrades, by β-elimination, the uronic acids of the permethylated polysaccharides.

The presence of acetic substituents was identified by liquid chromatography on an ion-exclusion column after hydrolysis of the 5T1 polysaccharide. The pyruvic group, probably linked to the galactose by an acetal bond on the 4 and 6 hydroxyls, was identified by methanolysis of the polysaccharide and of its permethylated derivative. The group R present on the lyxose was not characterised.

EXAMPLE 2

Stabilisation of artificial cements:

After storage for 8 days at room temperature or 4 days at 50° C., an aqueous composition containing 50% by weight of Portland-type cement and 1% of PS-5T1 polysaccharide remains homogeneous, malleable and exhibits only a slight surface hardening.

EXAMPLE 3

Cream dessert

Creams having the following composition are prepared:

|  | vanilla cream | chocolate cream |
| --- | --- | --- |
| skimmed milk powder | 3.5% by weight | 1.5% |
| Sugar | 10% | 12% |
| Starch | 1.7% | 1.7% |
| Cocoa | — | 3% |
| Vanilla flavouring | 0.3% | — |
| Stabilising agent* | 0.2% | 0.18% |
| Whole milk | qs 100 | qs 100 |

*Compound containing 65% (w/w) of carrageenan and 35% PS-5T1.

The ingredients, which are premixed while dry, are dispersed in the cold milk. After hydrating for 15 minutes, the mixture is passed over a plate exchanger and undergoes the following treatment:

pasteurisation at 90° C.

homogenisation at 50 kg/cm$^2$ sterilisation at 130° C.

cooling to 65° C.

It is then packaged.

In both cases, the final texture of the creams is thick, smooth, shiny and without air bubbles.

Control creams containing only carrageenan or xanthan as stabilising agent have a less homogeneous texture and appearance and exhibit bubbles: additionally, creams according to the invention flow better in the apparatuses.

EXAMPLE 4

Salad dressings:

Acidic salad dressings having the following composition are prepared:

| Tap water | 25.05% by weight |
| --- | --- |
| White vinegar 8° | 15.90% |

| | |
|---|---|
| Tomato purée (28%) | 3.60% |
| Salt | 4.20% |
| Pepper | 0.60% |
| Sugar | 10.40% |
| Soya oil | 40.00% |
| Stabilising agent* | 0.25% |

*stabilising agent: xanthan or PS-5T1 polysaccharide.

The stabilising agent is dispersed in the oil with stirring (mixture 1). The other dry ingredients are dispersed in the water with stirring (mixture 2). The vinegar is mixed with the tomato puré (mixture 3).

Mixtures 1, 2 and then 3 are introduced successively into a Herbort homogeniser and the mixture is then emulsified for 3 minutes under vacuum before being packaged and stored at room temperature.

The viscosities of the dressings were measured before packaging:

| | Brookfield Viscosity | Bostwick (14 cm) Flow time |
|---|---|---|
| Xanthan | 2 450 cps | 51 seconds |
| PS-5T1 | 2 800 cps | 94 seconds |

The dressing according to the invention is observed as being more stable during storage.

EXAMPLE 5

Toothpastes:

Toothpastes with the following composition are prepared:

| | |
|---|---|
| Na saccharin | 0.2% by weight |
| Na benzoate | 0.5% |
| Stabilising agent* | 1% |
| Na pyrophosphate | 0.25% |
| Glycerol | 22% |
| Calcium phosphate | 53% |
| Na lauryl sulphate | 1.5% |
| Flavouring | qs |
| Water | qs 100 |

*Stabilising agent: PS-5T1 polysaccharide or xanthan.

The saccharin, benzoate, PS-5T1 and pyrophosphate are firstly dispersed in the glycerol; the water is added after stirring for 5 minutes and the solution is then maintained in a water bath at 75° C. for 15 minutes. It is then poured onto the calcium phosphate with stirring; after 10 minutes, the lauryl sulphate and flavouring are poured into the mixture.

The toothpastes according to the invention have a pleasing texture with a smooth appearance, and they exhibit a viscosity which is stable and greater by approximately 30% than that obtained with a control which is stabilised with xanthan.

We claim:

1. A polysaccharide comprising repeating nonasaccharide units each of which has two D-mannose moieties, two D-glucose moieties, one D-galactose moiety, one D-xylose, one D-glucuronic acid, one L-lyxose moiety, and one L-fucose moiety, said polysaccharide being obtainable through a process comprising culturing Pseudomonas 5T1 CNCM No. I-1145 in an aerated fermentation nutrient medium including a carbon source, an organic nitrogen source, and growth factors at a temperature of between 20° C. and 32° C. and a pH of between 6.5 and 9, and precipitating with a water-miscible solvent selected from the group consisting of ethanol, methanol, isopropanol and acetone.

2. A polysaccharide according to claim 1, having a viscosity range of about 10.5–3000 mPa.s at a concentration of 10 g/l and at a shear rate of about 0.01–140 $s^{-1}$.

3. A polysaccharide according to claim 1, having a viscosity range of about 2–2000 mPa.s at a shear rate of 0.01 $s^{-1}$ and at a concentration of about 50–1000 ppm.

4. A polysaccharide according to claim 1, wherein the repeating nonasaccharide units have the formula

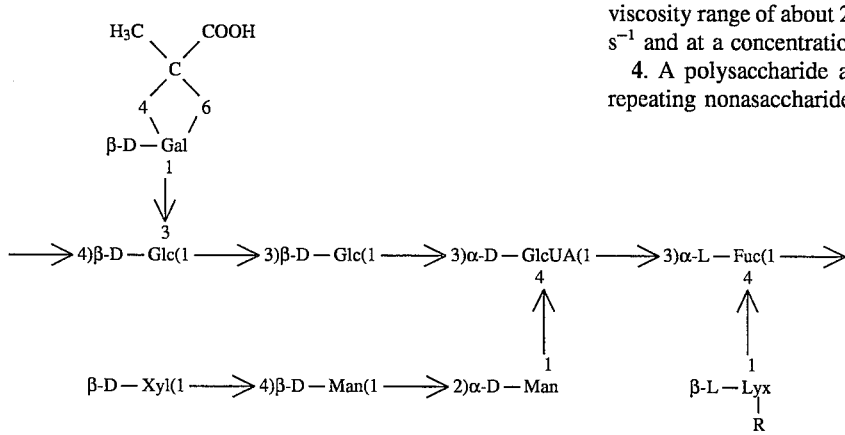

wherein R is H or a $C_1$–$C_6$ group.

5. A polysaccharide according to claim 4, wherein R is hydrogen.

6. A polysaccharide according to claim 4 wherein each nonasaccharide unit has three saccharide hydroxyl groups esterified to acetates.

* * * * *